United States Patent [19]
Nisbet et al.

[11] Patent Number: 5,340,577
[45] Date of Patent: Aug. 23, 1994

[54] PROBIOTIC FOR CONTROL OF SALMONELLA

[75] Inventors: David J. Nisbet; Donald E. Corrier; John R. DeLoach, all of College Station, Tex.

[73] Assignee: The United States of America, as represented by the Secretary of Agriculture, Washington, D.C.

[21] Appl. No.: 921,173

[22] Filed: Jul. 29, 1992

[51] Int. Cl.$^5$ .............................................. A61K 35/74
[52] U.S. Cl. ................. 424/93.21; 424/93.3; 424/93.4; 424/93.45
[58] Field of Search ................. 424/93 B, 93 C, 93 D, 424/93 J

[56] References Cited

U.S. PATENT DOCUMENTS 4,871,539  10/1989  Hata et al. .................... 424/93 C

OTHER PUBLICATIONS

Baba et al. Poult. Sci 1991 Sep; 701(9): 1902–1907.
Bilgili et al. Poult. Sci 1990 Oct; 69(10): 1670–1674.
Barrow et al. Epidemol Infect 1987 Jun; 98(3) 311–322.

*Primary Examiner*—Marianne M. Cintins
*Assistant Examiner*—K. Weddington
*Attorney, Agent, or Firm*—M. Howard Silverstein; Randall E. Deck; John D. Fado

[57] ABSTRACT

A defined probiotic or composition of anaerobic bacteria effective for controlling or inhibiting Salmonella colonization of fowl. The probiotic includes populations or cultures of substantially biologically pure bacteria, which bacteria include:
(a) at least one Lactobacillus species;
(b) one or both of:
  *Lactococcus lactis*, and
  *Citrobacter freundii*; and
(c) at least one of:
  one or more Enterococcus species,
  one or more Bifidobacterium species,
  one or more Propionibacterium species, and
  one or more Escherichia species.

In use, the probiotic is administered to the subject fowl in an amount effective for inhibiting Salmonella colonization thereof.

The invention also relates to a novel method for isolating probiotics which are effective for controlling or inhibiting Salmonella colonization of fowl, from fecal droppings or cecal contents of adult fowl. The droppings or cecal contents are combined with a culture medium and incubated without dilution (i.e. batch culture) under anaerobic conditions. Following this preliminary incubation, the resultant culture is subjected to continuous flow conditions until a steady state is achieved, after which time the steady state culture may be recovered for use as a probiotic.

27 Claims, No Drawings

PROBIOTIC FOR CONTROL OF SALMONELLA

BACKGROUND OF THE INVENTION

1. Field of Invention

This invention relates to a defined probiotic for the control of Salmonella colonization in fowl, particularly chickens.

Despite the efforts of researchers and public health agencies, the incidence of human salmonellosis has increased over the past 20 years. The number of actual reported cases of human Salmonella infection exceeds 40,000 per year. However, the Communicable Disease Center estimates that the true incidence of human Salmonella infections in the U.S. each year may be as high as 2 to 4 million. Animal food products, including poultry, remain the principal source of human infection.

2. Description of the Prior Art

Considering the widespread presence of Salmonella in the environment, it is unlikely that poultry can be completely protected from Salmonella exposure. Therefore, researchers have continued to investigate means of increasing resistance to colonization in poultry exposed to Salmonella. Studies have focused on the evaluation of vaccines, establishment of protective normal intestinal flora, and the identification of feed additives that will inhibit Salmonella growth and colonization. The role of host immunity against Salmonella colonization is unclear, and it also remains uncertain if stimulation of immune responses will effectively enhance colonization resistance. Experimental vaccines have not proven to be consistently effective.

It is well documented that normal intestinal microflora increase resistance against Salmonella colonization. Oral inoculation of young chicks with anaerobic bacterial cultures of microflora, also known as probiotics (defined as bacterial cultures which have a beneficial effect on the animal to which they are administered), prepared from the cecal contents or fecal droppings of mature chickens has proven to effectively reduce Salmonella colonization [Snoeyenbos et al., Avian Dis., 23:904–913, (1979), Schneitz et al., Acta Pathol. Microbiol. Scand. Sect. B., 89:109–116, (1981), and Stavric et al., J. Food Prot., 48:778–782, (1985)]. Conversely, poultry rearing practices that prevent chicks from becoming colonized by these cecal anaerobes make the chicks more susceptible to Salmonella colonization [Pivnick et al., J. Food Prot., 44:909–916, (1981)]. These probiotics may decrease Salmonella colonization by rapidly colonizing the intestinal tract of the young chicks (Pivnick et al., ibid), by competing for attachment sites on the intestinal wall (Snoeyenbos et al., ibid), or by producing bacteriostatic or bactericidal short-chained volatile fatty acids [Barnes et al., J. Hyg. Camb., 82:263–283, (1979) and Am. J. Clin. Nutr., 33:2426–2433, (1980), Corrier et al., Avian Dis., 34:668–676, (1990) and Avian Dis., 34:617–625, (1990), and Hinton et al., Avian Dis., 34:626–633, (1990)] that inhibit the growth of enteropathogens.

However, only cultures of normal microflora that contain a mixed population of several hundred different micro-organisms have proven to effectively inhibit Salmonella growth. Establishment of normal intestinal flora in day-old chicks using mixed cultures of microorganisms has been widely used to control Salmonella colonization in several European countries. Yet, because of the undefined number and types of microorganisms present in mixed cultures, the system has not been widely accepted in the United States. One drawback to the widespread use of this method has been the fact that the composition of the product cannot be standardized, and thus the product cannot be stored or produced on a large scale without changes in composition and effectiveness. Also, because the starting material is always the intestinal content of an adult fowl, the product may contain pathogenic viruses, bacteria, or parasites, which may be dangerous to the health of the chicks. Further still, the U.S. Food & Drug Administration has recently required that all undefined cultures must be approved.

Lactose and other milk sugar products added to the feed or water of chicks have recently been reported to enhance resistance against Salmonella colonization [Oyofo et al., Avian Dis., 33:531–534, (1989) and Poultry Sci., 68:1357–1360, (1989), Corrier et al., ibid, and Hinton et al., ibid.]. Dietary lactose increases the acidity of the cecal contents and influences the growth and fermentation products of normal intestinal microflora. Lactose supplemented diets may also enhance Salmonella colonization resistance by increasing the bacteriostatic action of short chain volatile fatty acids such as acetic, propionic, and butyric acids, produced by some normal intestinal bacteria [Corrier et al., ibid, Hinton et al., ibid].

Resistance to Salmonella colonization in chicks has also further been increased when the chicks are provided the combination of dietary lactose and cultures of cecal anaerobes grown in a lactose containing broth [Corrier et al., ibid, Hinton et al., ibid].

SUMMARY OF THE INVENTION

We have now discovered a defined probiotic or composition of bacteria effective for controlling or inhibiting Salmonella colonization of fowl. The probiotic includes populations or cultures of substantially biologically pure bacteria, which bacteria include:
- (a) at least one Lactobacillus species;
- (b) one or both of:
  - *Lactococcus lactis* (formerly referred to as *Streptococcus lactis*), and
  - *Citrobacter freundii*; and
- (c) at least one of:
  - one or more Enterococcus species,
  - one or more Bifidobacterium species,
  - one or more Propionibacterium species, and
  - one or more Escherichia species.

In use, the probiotic is administered to the subject fowl in an amount effective for inhibiting Salmonella colonization thereof. In a preferred embodiment, enhanced inhibition of Salmonella may be achieved by incorporation of lactose into the probiotic. The above-mentioned probiotic may also be combined with a conventional feed, providing a novel feed product which may be orally ingested by the fowl.

The invention also relates to a novel method for isolating probiotics which are effective for controlling or inhibiting Salmonella colonization of fowl, from fecal droppings or cecal contents of adult fowl. The droppings or cecal contents are combined with a nutrient or culture medium and incubated without dilution (i.e. batch culture) under anaerobic conditions. Following this preliminary incubation, the resultant culture is subjected to continuous flow conditions until a steady state is achieved, after which time the steady state culture may be recovered for use as a probiotic.

In accordance with this discovery, it is an object of this invention to provide an improved method and composition for controlling Salmonella colonization in fowl.

A further object of this invention is to provide defined cultures of anaerobic bacteria for controlling Salmonella colonization in fowl which may be easily standardized.

Yet another object is to provide an improved method for isolating compositions of bacteria for use as probiotics for controlling Salmonella colonization in fowl.

Other objects and advantages of this invention will become obvious from the ensuing description.

DETAILED DESCRIPTION OF THE INVENTION

The probiotic of this invention is effective for controlling Salmonella colonization of fowl when administered thereto, reducing the average Salmonella concentration in the fowl population and/or lowering the percentage fowl colonized by the pathogen. The invention may be practiced with any type of fowl, including but not limited to poultry such as chickens, turkeys, ducks, quail and geese. Upon administration to fowl, the probiotic provides consistent protection against a variety of Salmonella, especially *S. typhimurium* and *S. enteriditis*.

Suitable bacteria utilized in the probiotic include substantially biologically pure bacteria of the genera Lactobacillus, Enterococcus, Bifidobacterium, Propionibacterium and Escherichia, in combination with one or both of *Lactococcus lactis* and *Citrobacter freundii*. Of these bacteria, under anaerobic culture conditions the lactobacilli, enterococci, escherichiae, *Lactococcus lactis* and *Citrobacter freundii* should be effective for fermenting carbohydrates to produce lactic acid, while the bifidobacteria and propionibacteria should be effective for producing volatile organic acids including acetic, propionic, and/or butyric acids.

Without being limited thereto, preferred lactobacilli include *L. animalis* and *L. acidophilus*; preferred enterococci include *E. faecalis* and *E. avium*; preferred escherichiae include *E. coli* and *E. fergusonii*; preferred bifidobacteria include *B. animalis*; and preferred propionibacteria include *P. acidipropionici*. However, it is understood that other species and/or strains of these bacteria may be utilized, and suitable alternatives may be selected for their ability to produce lactic acid or one or all of the above-mentioned volatile organic acids, using the techniques described by DeLoach et al. ["Probiotic for Control of Salmonella", U.S. patent application Ser. No. 07/822,505, filed Jan. 17, 1992, the contents of which are incorporated by reference herein] or Hinton et al. [J. Food Prot., vol. 54, no. 7, pages 496–501, July, 1991, the contents of which are also incorporated by reference herein]. The bacteria also should not produce bacteriocins effective against the other above-mentioned bacteria of the probiotic.

Each of the bacteria to be used may be obtained from representative or known species and strains, or in a preferred embodiment, they may be individually isolated and recovered from fecal droppings or cecal contents of adult fowl using techniques conventional in the art or as described by DeLoach [U.S. patent application Ser. No. 07/822,505]. In accordance with the first-mentioned method, when stock cultures of known strains are used, improved results may be achieved by adapting the bacteria to the fowl by passage therethrough, followed by their subsequent retrieval and isolation from droppings or cecal contents. In another preferred embodiment, the probiotic may be obtained from fecal droppings or cecal contents of adult fowl by continuous culture in a chemostat as described hereinbelow and in Example 1. The resultant steady state culture may be used directly as a probiotic, or the individual bacteria may be isolated for ease of storage and subsequently recombined.

It is envisioned that this invention may be practiced with a probiotic having as few as three different bacteria, i.e. a single Lactobacillus species, one of *Lactococcus lactis* or *Citrobacter freundii*, and only one Enterococcus, Bifidobacterium, Propionibacterium or Escherichia species. However, in accordance with a preferred embodiment, enhanced control of Salmonella is achieved with a probiotic which includes both Enterococcus and Bifidobacterium species. An especially preferred probiotic further includes Propionibacterium and Escherichia species and both of the *Lactococcus lactis* and *Citrobacter freundii* as well. Surprisingly, the probiotic of Example 1 also exhibits significant stability under continuous culture conditions, and is particularly preferred.

Some or all of the strains of the bacteria of this invention may also be optionally selected for the ability to adhere to the epithelial cells of the alimentary tract of the subject fowl in accordance with the technique of Nurmi et al, U.S. Pat. No. 4,689,226, the contents of which are incorporated by reference herein.

In one embodiment, the probiotic of this invention may be obtained by batch or continuous propogation of the bacteria in a suitable culture medium using anaerobic culture techniques conventional in the art. As mentioned hereinabove, the inoculum for the culture may be from stock cultures or substantially biologically pure isolates of the bacteria. The bacteria may be cultured in combination, or in separate culture media and subsequently combined for ease of standardization. In accordance with the latter technique, the final concentration of each bacteria should be between about $10^8$ to $10^9$ organisms/ml prior to combination. However, the practitioner skilled in the art will recognize that the concentration is not critical and may vary.

Rather than producing a probiotic from known stock cultures or pure bacterial isolates as described hereinabove, we have unexpectedly discovered that a stable, defined probiotic may also be produced directly from fecal droppings or cecal contents of adult fowl. In accordance with this method, the droppings or cecal contents are first used as inoculum for a batch culture, and then cultured under continuous flow conditions at specified media turnover and pH until a steady state or equilibrium is attained. The resultant steady state culture may be recovered for use as a probiotic.

The batch culture stage may be conducted in any conventional fermenter. However, use of a chemostat without dilution (i.e. without addition of fresh culture medium and removal of spent culture medium) is preferred to eliminate transfer of the culture for subsequent steps, and to reduce potential contamination of the culture. After their collection, the cecal contents from fowl or their droppings, which are to be used as inoculum, are combined with a suitable culture medium and incubated under anaerobic conditions. This batch culture should be continued:

(1) for about 12–18 hours, or
(2) until the optical density (measured at 600 nm) reaches at least about 1.0, and/or (3) for no more than about 2 hours after the pH reaches about 4.2;

after which time the batch culture should be terminated and continuous culture initiated. When the incubation period is determined by condition (1) or particularly condition (2), it is preferred to control the pH at about 5.5 using a pH controller as is conventional in the art. Further, in the event that this pH control is not employed, to avoid death of some of the cells, it is preferred that the batch culture should be continued to a pH no less than about 4.2.

Continuous culture in a chemostat, with continuous supply of fresh medium and removal of spent broth, is then initiated immediately following conclusion of the batch culture stage. Suitable chemostats may be readily determined and include, for example, those described by Wang [Fermentation and Enzyme Technology, John Wiley & Sons, New York, 1979, pages 98–137, the contents of which are incorporated by reference herein]. Surprisingly, growth of the mixture in continuous culture with a specific dilution or media turnover rate and at a specific pH allows the culture to come to an equilibrium or steady state. Depending upon the fowl used as the inoculum source, the specific media and culture conditions, the approximately 500 bacteria originally present may be reduced to a stable culture of about 10 to 20 substantially biologically pure bacteria which may be readily defined. Suitable conditions for this stage include a turnover rate between about 0.029 to about 0.10 $hr^{-1}$, preferably about 0.0416 $hr^{-1}$, and a pH between about 4.7 to 6.5, preferably about 5.5.

The temperature and media used for the batch and continuous cultures are not critical and may be readily determined. Suitable temperatures may vary between about 26° to 47° C. A variety of suitable culture media having different energy sources may also be used. Without being limited thereto, preferred energy sources include glucose or galactose and particularly lactose.

Once a steady state is achieved, the culture may be recovered at any time for use as described. Ideally, the steady state culture should also be characterized or defined, isolating and identifying the bacterial populations therein using techniques conventional in the art. Once isolated, the bacteria may be stored indefinitely using conventional techniques for later use as described, for instance, in Example 4. The practitioner skilled in the art will recognize that the above-described batch-/continuous culture process may also be employed using isolated or biologically pure bacteria as initial inoculum.

The use of the probiotic of this invention is not affected by the particular method of production; probiotic produced by any of the above-described methods may be used in the same manner. Following propogation, the cultures of bacteria may be administered directly to the subject fowl singly or in combination. Optionally, the probiotic may be further formulated with a suitable carrier including, but not limited to lactose or skim milk, or combined with a small amount of feed for use as a premix. The cultures may also be freeze dried for storage stability and ease of handling. Such freeze dried cultures may be directly administered to the fowl or, in the alternative, reconstituted prior to use. Of special note, one or all of the bacteria may be encapsulated using techniques conventional in the art, including, but not limited to encapsulation in an alginate gel. Without wishing to be bound by theory, it is believed that encapsulation in this manner may prevent same bacteria from reducing the concentration of lactic acid in the upper intestinal tract to undesirable levels. It may also protect the bacteria and allow them to reach the ceca, where lactic acid utilization is desirable.

The probiotic of this invention may also be combined with other substantially biologically pure bacteria which are used in probiotics effective for control of Salmonella in fowl. Without being limited thereto, other suitable bacteria include Peptostreptococcus species, or those described in DeLoach [U.S. patent application Ser. No. 07/822,505], especially Veillonella species. Other adjuvants conventional or known in the art for the treatment of fowl, and particularly for the inhibition of enteropathogens, may be added to the probiotic. Suitable adjuvants include, for example, coccidiostats that are not effective against gram positive organisms. Addition of lactose is especially preferred.

Non-therapeutic levels of antibiotics may also be administered to the fowl as is conventional in the art. Such antibiotics may be administered in combination with or apart from the probiotic. Alternatively, these antibiotics may be administered in ovo at levels which are therapeutic, but which decline to non-therapeutic levels within about 3 days after hatching.

While the probiotic of this invention is primarily administered or introduced to the alimentary tract by combining with the feed or water of the fowl followed by oral ingestion thereof, it is envisioned that it may also be administered orally and nasally by spraying or misting the formulation directly upon the fowl as is conventional in the art. Still other alternatives include injection directly into the gastrointestinal tract, or administration cloacally. In regard to the latter, the probiotic may be sprayed directly onto the anus of the fowl or applied to the pen floor litter whereupon it will contact the anal area through the course of normal activity of the fowl. Once contacted with the anal area, the probiotic will be introduced into the cloaca by reverse peristalsis.

Administration of the probiotic may be at any time during the life of the fowl. However, in the preferred embodiment the probiotic is administered to newly hatched fowl between about 1 to 14 days old.

The probiotic is administered in an amount effective to substantially inhibit the Salmonella colonization in the treated fowl, in comparison with untreated fowl. Suitable amounts may be readily determined by the practitioner skilled in the art, and will vary somewhat with the age and size of the animal.

The following examples are intended only to further illustrate the invention and are not intended to limit the scope of the subject matter which is defined by the claims.

EXAMPLE 1

Preparation of Probiotic

Initial Innoculum

The initial innoculum was obtained from a mature broiler (reared at the USDA-FAPRL in College Station, Tex.) maintained on a typical broiler ration plus 5% lactose in the feed (w/w). This bird was taken from a flock of mature broilers in which protective cecal microflora had been maintained over a period of 2 years. The bird was sacrificed and the ceca were removed and immediately transferred into a Coy Glove Box anaerobic chamber (Coy Laboratory Products, Ann Arbor, Mich.). The cecal contents were emptied into a sterile test tube and mixed with 5 parts glycerine and stored at −70° C. Prior to mixing with glycerine ca. 1 g of cecal material was inoculated into 100 mls of Viande Levure broth (media pH=5.50) and incubated at 39° C. for 18 hours. All procedures were performed under anaerobic and sterile conditions.

Continuous Flow Apparatus

When the culture was grown under continuous flow conditions the following parameters were used. A Bio-Flo 1 fermenter (New Brunswick Scientific) fitted with a 2 L chemostat vessel (Weir type) with a 1150 ml working volume at a dilution rate of 0.0416 h$^{-1}$; temperature=39° C.; agitation speed=200 RPM. Anaerobic conditions were maintained by flushing the vessel with a constant stream of $O_2$-free $CO_2$.

Continuous Flow Media

A modified Viande Levure (VL) broth medium was used (Media pH=5.50). Media was prepared in a 13.3 L Pyrex glass vessel and autoclaved at 15 psi for 1.5 hours. After sterilization, media was immediately put under an atmosphere of $O_2$-free $CO_2$ and allowed to cool to room temperature.

| Media Component | Concentration (g/l) |
| --- | --- |
| tryptose | 10 |
| yeast extract | 5 |
| NaCl | 5 |
| beef extract | 2.4 |
| L-cysteine HCl | .6 |
| Lactose | 2.5 |

Growth of Cecal Organisms Under Continuous Flow Conditions

The 1150 ml working volume chemostat vessel was filled with 1100 mls of VL broth and allowed to sit for 24 hours prior to inoculation to ensure no microbial contamination of the media had occurred. After 24 hours, the vessel was inoculated with 50 mls of the original batch grown cecal organisms (culture $OD_{600}=1.0$; pH=5.0). Samples were taken at 2 hour intervals to monitor culture pH, optical density ($OD_{600}$) and volatile fatty acid concentrations. After 18 hours the culture $OD_{600}$ and pH were 0.875 and 4.26, respectively. At this time the culture was switched to continuous flow conditions. After 5 days of continuous flow culture, steady state conditions were achieved. Steady state conditions were assumed when culture pH, $OD_{600}$ and volatile fatty acid concentrations remained relatively constant (Table 1).

The steady state culture, designated CFII, consisted of eleven different bacteria, including four facultative anaerobic gram-positive cocci, two facultative anaerobic gram-positive bacilli, three facultative anaerobic gram-negative bacilli, one obligate anaerobic gram-positive bacillus, and one obligate anaerobic gram-positive coccobacillus. The bacteria were identified as:
Enterococcus faecalis (designated strain A),
Enterococcus faecalis (designated strain B),
Enterococcus avium,
Lactococcus lactis,
Lactobacillus species (designated CMS),
Lactobacillus animalis,
Citrobacter freundii,
Escherichia coli,
Escherichia fergusonii,
Bifidobacterium animalis, and
Propionibacterium acidipropionici.

EXAMPLE 2

In Vivo Experiments with Broiler Chicks and S. typhimurium

Experimental Design

One-day-old broiler chicks were separated into 4 groups. Treatments included 1) control diet, 2) 5% lactose diet, 3) CFII culture from Example 1+ control diet, and 4) CFII culture from Example 1+5% lactose diet. Birds receiving the CFII culture were orally gavaged with 0.50 mls (approximately $5\times10^8$ total organisms) on day 1. On day 3, all birds were challenged by crop gavage with $10^4$ S. typhimurium. Seven days later (day 10), chicks were killed by cervical dislocation and cecum contents were analyzed for pH, CFU S. typhimurium, VFAs', and lactic acid. The experiment was replicated 4 times over a period of 103 days of steady state conditions of the CFII culture. Data is reported as follows: Trial 1=8-day-old CFII; Trial 2=59-day-old CFII; Trial 3=73 day-old CFII; and Trial 4=103-day-old CFII.

Results

During the 103 day period of continuous culture, the average $\log_{10}$ decrease (across 4 trials) in S. typhimurium cecal colonization was 2.11 and 4.06 for the CFII culture alone and the CFII culture+lactose respectively (Table 2). No differences were observed in VFA or lactic acid concentrations (data not shown) with the exception of higher cecal propionate concentrations observed in experiments 2 and 3 for the CFII and CFII+lactose treated birds (Table 3). Cecal pH was lower in all cases for the lactose treated birds and in experiments 2, 3 and 4 the CFII+lactose treated birds had lower cecal pH values ($P<0.05$) than the lactose only treated birds (Table 4). No differences in mortality rate were observed in either treatments containing the CF cultures (Table 5).

EXAMPLE 3

In Vivo Experiments with Layer Chicks and S. enteritidis

Experimental Design

The same design was used with the layer chicks as previously described in Example 2 with these noted exceptions, S. enteritidis was substituted for S. typhimurium. Additional selenite-cysteine organ culture data is included as well as percent cecal positive birds. The same CFII culture was used, however, the age of culture differed. Trial 1 CFII= 79-day-old; Trial 2 CFII=100-day-old; Trial 3 CFII=130-day-old; and Trial 4 CFII=135 day old.

Results

A large decrease in percent cecal S. enteritidis positive birds were observed in all trials in the presence of the culture+lactose. Lactose alone also decreased the number of cecal positive birds but not to the same extent as when the culture was included in the treatment (Table 6). Percent organ culture positive birds (Table 7) was decreased both in the presence of lactose and lactose+CFII. The culture by itself also tended to decrease the percent organ culture positive birds. In all four trials, a significant decrease in $\log_{10}$ CFU S. enteri-

*tidis* (SE) was observed in the lactose+CFII treated groups (Table 8). In experiments 2, 3 and 4, lactose alone decreased $\log_{10}$ CFU of SE, however, in all cases it appears that the addition of the culture further enhances the protective effect of lactose. The data in Table 9 indicates that no differences in mortality was found either due to lactose or the culture across all experiments.

EXAMPLE 4

Preparation of Probiotic

The 11 bacterial species previously isolated from the continuous flow culture in Example 1 were individually grown in pure culture using standard bacteriological medias, then lyophilized and stored at −70° C. After 60 days of storage the lyophilized cultures were reconstituted in anaerobic Viande Levure broth media modified to contain 0.25% glucose and 0.25% lactose and grown in pure culture under anaerobic conditions to an optical density of 1.0. To reconstruct the mixed defined culture, 90 mls of each of the pure culture isolate fermentations was used to inoculate a chemostat vessel, and this subsequent mixed culture was grown under continuous flow conditions as described in Example 1.

After steady state conditions were reached, the culture was examined for the presence of individual isolates and contaminants. All eleven isolates were isolated from the steady state culture and no contaminants were found.

A second steady state culture was prepared by the same method described above, except that the *E. coli* and *E. fergusonii* were deleted.

EXAMPLE 5

Reduction of Cecal Colonization by Salmonella

Three week old steady state cultures from Example 4 were examined for their efficiency in reducing cecal colonization by Salmonella using the same procedure described in Example 2. The results are shown in Table 10. There was no mortality due to the cultures, and similar levels of *S. typhimurium* colonization were evidenced as with CFII in Example 2.

It is understood that the foregoing detailed description is given merely by way of illustration and that modifications and variations may be made therein without departing from the spirit and scope of the invention.

TABLE 1

| | | | | Chemostat Data CFII (Lactose Media) | | | | | |
|---|---|---|---|---|---|---|---|---|---|
| S# | Time | OD600 | pH | HAC | HPR | HBU | HIBU | HVA | HIV | LACTATE |
| 1 | B2H | 0.24 | 5.48 | 1.07 | 0.52 | 0.5 | 0.13 | 0.07 | 0.06 | 36.2 |
| 2 | B6H | 0.756 | 4.58 | 1.34 | 0.53 | 0.5 | 0.14 | 0.07 | 0.06 | 145.1 |
| 3 | B18 | 0.875 | 4.26 | 2.43 | 0.46 | 0.4 | 0.1 | | 0.03 | 212.1 |
| START CONTINUOUS FLOW | | | | | | | | | | |
| 4 | CFD1 | 0.88 | 4.36 | 2.95 | 0.43 | 0.4 | 0.09 | | | 192.3 |
| 5 | D2 | 0.72 | 4.64 | 5.47 | 0.42 | 0.3 | | | | 134.5 |
| 6 | D3 | 0.62 | 4.75 | 6.44 | 0.42 | 0.3 | | | | 104.5 |
| 7 | D4 | 0.62 | 4.89 | 5.46 | 0.47 | 0.3 | | | | 115.4 |
| 8 | D5 | 0.895 | 5.3 | 11.6 | 12.3 | 0.3 | | | | 5.3 |
| 9 | D6 | 0.895 | 5.3 | 13.7 | 14.6 | 0.3 | | | | 5.6 |
| 10 | D7 | 0.895 | 5.21 | 11.8 | 9.74 | 0.3 | 0.17 | 0.05 | 0 | 4.9 |
| 11 | D8 | 0.895 | 5.21 | 16.1 | 12.9 | 0.3 | 0.19 | | | 5.7 |
| 12 | D9 | 0.945 | 5.15 | 12.3 | 9.88 | 0.3 | 0.14 | | | 4 |
| 13 | D10 | 0.945 | 5.12 | 15.1 | 12.7 | 0.3 | 0.15 | | 0.01 | 8.8 |
| 14 | D11 | 0.985 | 5.3 | 14.9 | 15.8 | 0.3 | 0.15 | | | 13.2 |
| 15 | D12 | 0.985 | 5.3 | 13 | 13.8 | 0.3 | 0.14 | | | 9.3 |
| 16 | D13 | 0.985 | 5.3 | 18.2 | 18.7 | 0.6 | 0.24 | 0.01 | 0.12 | 5.9 |
| 17 | D14 | 0.985 | 5.3 | 17 | 17.4 | 0.5 | 0.24 | | 0.09 | 3.8 |
| 18 | D15 | 0.985 | 5.3 | 17.7 | 17.8 | 0.4 | 0.22 | | 0.07 | 3.9 |
| 19 | D16 | 1 | 5.28 | 15.9 | 14.9 | 0.4 | 0.25 | 0.03 | 0.07 | 2.9 |
| 20 | D35 | 1.2 | 5.5 | 17.8 | 9.97 | 1 | 1.99 | 0.29 | 0.38 | 8.6 |
| 21 | D40 | 1.23 | 5.6 | 17.9 | 9.69 | 1.3 | 2.02 | 0.28 | 0.49 | 7.5 |
| 22 | D54 | 1.24 | 5.53 | 22.3 | 11 | 1.2 | 2.28 | 0.22 | 0.44 | 4.4 |
| 23 | D60 | 1.24 | 5.55 | 14.3 | 7.02 | 0.7 | 1.73 | 0.18 | 0.43 | 3.9 |
| 24 | D66 | 1.2 | 5.46 | 13.3 | 7.01 | 0.7 | 1.62 | 0.21 | 0.33 | 5.9 |
| 25 | D73 | 1.2 | 5.55 | 18.6 | 10.2 | 1.6 | 2.36 | 0.35 | 0.59 | 9.6 |
| 26 | D80 | 1.2 | 5.5 | 20.2 | 10.6 | 1.6 | 2.3 | 0.36 | 0.43 | 5.4 |
| 27 | D87 | 1.2 | 5.51 | 19.3 | 10.1 | 1.5 | 2.19 | 0.34 | 0.41 | 5.1 |
| 28 | D94 | 1.2 | 5.5 | 17.5 | 11.8 | 0.9 | 2.11 | 0.3 | 0.37 | 4.5 |
| 29 | D101 | 1.2 | 5.47 | 14 | 10.1 | 0.9 | 1.66 | 0.34 | 0.26 | 3.3 |
| 30 | D121 | 1.24 | 5.55 | 20.5 | 11.1 | 1.3 | 2.39 | 0.44 | 0.26 | 5.7 |
| 31 | D143 | 1.36 | 5.55 | 15.2 | 8.36 | 1 | 1.8 | 0.33 | 0.4 | 2.9 |

LEGEND
S# = Sample Number
TIME- B = Batch Phase of Culture
D = Day of Continuous Flow Culture
OD600 = Optical Density of Culture
pH = Culture pH
HAC = Acetate (UMOL/ML)
HPR = Propionate (UMOL/ML)
HBU = Butyrate (UMOL/ML)
HIBU = Isobutyrate (UMOL/ML)
HVA = Valerate (UMOL/ML)
HIV = Isovalerate (UMOL/ML)
LACTATE = Lactate (UMOL/ML)

TABLE 2

| Effect of CFII on Cecal Colonization by *S. Typhimurium* | | | | |
|---|---|---|---|---|
| | Average log *S. typhimurium*/gram cecal contents | | | |
| Treatment | Trial 1 | Trial 2 | Trial 3 | Trial 4 |
| Control (C) | 4.09$^a$ | 6.93$^a$ | 7.00$^a$ | 7.05$^a$ |
| Lactose (L) | 2.29$^a$ | 5.15$^b$ | 6.10$^a$ | 4.77$^b$ |
| CFII + C | 1.95$^b$ | 2.06$^c$ | 6.63$^a$ | 6.00$^a$ |

TABLE 2-continued

Effect of CFII on Cecal Colonization by S. Typhimurium

Average log S. typhimurium/gram cecal contents

| Treatment | Trial 1 | Trial 2 | Trial 3 | Trial 4 |
|---|---|---|---|---|
| CFII + L | 1.07[b] | 1.34[c] | 3.15[b] | 3.27[b] |

[a,b,c] Values in columns with different superscripts differ $P < .05$.

TABLE 3

Effect of CFII on Cecal Propionate

Cecal Propionate Concentration (umol/ml)

| Treatment | Trial 1 | Trial 2 | Trial 3 | Trial 4 |
|---|---|---|---|---|
| Control (C) | 8.32[a] | .98[a] | 3.44[a] | 8.59[a] |
| Lactose (L) | 8.84[a] | .42[a] | .96[a] | 11.00[a] |
| CFII + C | 8.33[a] | 32.20[b] | 3.50[a] | 10.32[a] |
| CFII + L | 7.67[a] | 34.23[b] | 26.05[b] | 10.18[a] |

[a,b,c] Values in columns with different superscripts differ $P < .05$.

TABLE 4

Effect of CFII on Cecal pH

Cecal pH

| Treatment | Trial 1 | Trial 2 | Trial 3 | Trial 4 |
|---|---|---|---|---|
| Control (C) | 5.95[a] | 5.55[a] | 5.80[a] | 6.20[a] |
| Lactose (L) | 5.37[b] | 5.29[b] | 5.32[b] | 5.62[b] |
| CFII + C | 5.53[b] | 5.44[a,b] | 5.76[a] | 5.91[a] |
| L + CF | 5.33[b] | 5.02[c] | 5.04[c] | 5.28[c] |

[a,b,c] Values in columns with different superscripts differ $P < .05$.

TABLE 5

Effect of CFII On Mortality in Broiler Chicks

% Mortality

| Group | Trial #1 | Trial #2 | Trial #3 | Trial #4 |
|---|---|---|---|---|
| Control (C) | 2/20 = (10%) | 1/20 (5%) | 0/20 (0%) | 2/20 (10%) |
| Lactose 5% (L) | 0/20 = (0%) | 1/20 (5%) | 1/20 (5%) | 0/20 (0%) |
| CFII + C | 0/20 (0%) | 0/20 (0%) | 1/20 (5%) | 0/20 (0%) |
| CFII + L | 0/20 (0%) | 1/20 (5%) | 0/20 (0%) | 0/20 (0%) |

TABLE 6

Effect of CFII Cultures on Salmonella enteritidis Colonization of Layer Chicks Salmonella Cecal Culture Positive/Total (%)[A]

| Group | Trial #1 | Trial #2 | Trial #3 | Trial #4 |
|---|---|---|---|---|
| Control | 14/20(70) | 20/20(100) | 19/20(95) | 18/20(90) |
| Lactose | 14/20(70) | 5/20(25)** | 12/20(60)** | 11/20(55)* |
| CFII | 12/20(60) | 17/19(90) | 16/20(80) | 10/20(50)* |
| CFII + Lactose | 0/20(0)** | 2/20(10)** | 7/20(35)** | 6/20(30)** |

[A] Selenite-cysteine-BGA-cultures
Significantly different from controls: * = $(P < 0.05)$; ** = $(P < 0.01)$.

TABLE 7

Effect of CFII Cultures on Salmonella enteritidis Colonization of Layer Chicks Salmonella Organ Culture Positive/Total (%)[A]

| Group | Trial #1 | Trial #2 | Trial #3 | Trial #4 |
|---|---|---|---|---|
| Control | 7/20(35) | 19/20(95) | 18/20(90) | 12/20(60) |
| Lactose | 4/20(20) | 1/20(5)** | 5/20(25)** | 2/20(10)** |
| CFII | 7/20(35) | 13/20(65)* | 6/20(30)** | 2/20(10)** |
| CFII + Lactose | 1/20(5)* | 1/20(5)** | 5/20(25)** | 1/20(5)* |

[A] Combined Spleen/Liver Cultures-Tetrathionate + BGA Cultures
Significantly different from controls: * = $(P < 0.05)$; ** = $(P < 0.01)$

TABLE 8

Effect of CFII Cultures on Salmonella enteritidis Colonization of Layer Chicks $Log_{10}$ Salmonella/gram Cecal Content[A]

| Group | Trial #1 | Trial #2 | Trial #3 | Trial #4 |
|---|---|---|---|---|
| Control | 3.93 ± 3.23 | 6.44 ± 1.40 | 5.61 ± 2.31 | 5.22 ± 2.69 |
| Lactose | 4.07 ± 3.16 | 0.93 ± 2.15** | 3.00 ± 2.85** | 2.15 ± 2.61** |
| CFII | 3.49 ± 3.21 | 5.72 ± 2.62 | 4.02 ± 3.02 | 2.73 ± 3.21** |
| CFII + Lactose | 0 ± 0** | 0.49 ± 1.57** | 1.59 ± 2.68** | 1.24 ± 2.30** |

[A] BGA dilution plates at 1:100; 1:1000; 1:10,000
Significantly different from controls: ** = $(P < 0.01)$.

TABLE 9

Effect of CFII On Mortality in Layer Chicks

% Mortality

| Group | Trial #1 | Trial #2 | Trial #3 | Trial #4 |
|---|---|---|---|---|
| Control | 1/25 (4%) | 0/20 (0%) | 0/25 (0%) | 0/25 (0%) |
| Lactose 5% (L) | 0/25 (0%) | 1/25 (4%) | 1/25 (0%) | 0/25 (0%) |
| CFII + C | 0/25 (0%) | 0/25 (0%) | 1/25 (0%) | 0/25 (0%) |
| CFII + L | 0/25 (0%) | 0/25 (0%) | 0/25 (0%) | 0/25 (0%) |

TABLE 10

| TREATMENT | $Log_{10}$ Salmonella per Gram Cecal Contents | % Chicks Salmonella-Positive | Chick Mortality (%) |
|---|---|---|---|
| Control | 3.64 +/− 2.15 | 14/15 (93%) | 0 |
| Lactose (5%) | 2.33 +/− 2.43 | 9/15 (67%) | 0 |
| [1]CF1 + C | 4.65 +/− 2.72 | 12/15 (80%) | 0 |
| [2]CF2 + C | 3.85 +/− 2.66 | 11/15 (73%) | 0 |
| [3]CF3 + C | 2.61 +/− 2.43 | 10/15 (67%) | 0 |
| [4]CF1 + L | 1.98 +/− 2.91 | 5/15 (33%) | 0 |
| [5]CF2 + L | 2.96 +/− 3.06 | 9/15 (67%) | 0 |
| [6]CF3 + L | 1.07 +/− 2.06 | 5/15 (33%) | 0 |

[1]CF + C = the original defined culture given to birds on control feed.
[2]CF2 + C = the recombined culture given to birds on control feed.
[3]CF3 + C = the recombined culture (minus E. coli and E. fergusonii) given to birds on control feed.
[4]CF1 + L = the original defined culture given to birds on lactose feed.
[5]CF2 + L = the recombined culture given to birds on lactose feed.
[6]CF3 + L = the recombined culture (minus E. coli and E. fergusonii) given to birds on lactose feed.

We claim:

1. A composition for inhibiting Salmonella colonization of fowl comprising populations of substantially biologically pure bacteria, said bacteria comprising:
   (a) at least one lactobacillus species;

(b) one or both of:
   *Lactococcus lactis*, and
   *Citrobacter freundii*; and
(c) at least one of:
   one or more Enterococcus species,
   one or more Bifidobacterium species,
   one or more Propionibacterium species, and
   one or more Escherichia species.

2. A composition as described in claim 1 wherein said bacteria comprise:
   one or more of said Enterococcus species, and
   one or more of said Bifidobacterium species.

3. A composition as described in claim 2 wherein said bacteria comprise both said *Lactococcus lactis* and said *Citrobacter freundii*.

4. A composition as described in claim 1 wherein said bacteria comprise:
   one or more of said Enterococcus species,
   one or more of said Bifidobacterium species, and
   one or more of said Propionibacterium species.

5. A composition as described in claim 4 wherein said bacteria comprise both said *Lactococcus lactis* and said *Citrobacter freundii*.

6. A composition as described in claim 1 wherein said bacteria comprise:
   one or more of said Enterococcus species,
   one or more of said Bifidobacterium species,
   one or more of said Propionbacterium species, and
   one or more of said Escherichia species, and both said *Lactococcus lactis* and said *Citrobacter freundii*.

7. A composition as described in claim 6 wherein:
   said Lactobacillus species comprises *Lactobacillus animalis* and one Lactobacillus species other than *Lactobacillus animalis*,
   said Enterococcus species comprises *Enterococcus faecalis* and *Enterococcus avium*,
   said Bifidobacterium species comprises *Bifidobacterium animalis*,
   said Propionibacterium species comprises *Propionibacterium acidipropionici*, and
   said Escherichia species comprises *Escherichia coli* and *Escherichia fergusonii*.

8. A composition as described in claim 1 further comprising one or more substantially biologically pure Veillonella species.

9. A composition as described in claim 1 further comprising one or more substantially biologically pure Peptostreptococcus species.

10. A composition as described in claim 1 further comprising lactose.

11. A composition as described in claim 1 further comprising a coccidiostat that is not active against gram positive bacteria.

12. A composition as described in claim 1, further comprising a carrier.

13. A composition as described in claim 1, wherein said bacteria are encapsulated.

14. A feed product comprising an animal feed in combination with said composition of claim 1.

15. A method for inhibiting Salmonella colonization of fowl comprising administering to said fowl a composition including populations of substantially biologically pure bacteria, said bacteria comprising:
   (a) at least one Lactobacillus species;
   one or both of:
      *Lactococcus lactis*, and
      *Citrobacter freundii*; and
   (c) at least one of:
      one or more Enterococcus species,
      one or more Bifidobacterium species,
      one or more Propionibacterium species, and
      one or more Escherichia species;
said bacteria administered in an amount effective for inhibiting Salmonella colonization of the intestine of said fowl.

16. A method as described in claim 15, wherein said fowl are poultry.

17. A method as described in claim 16, wherein said poultry are selected from the group consisting of chickens, turkeys, ducks, quail and geese.

18. A method as described in claim 16, wherein said poultry are less than about 14 days old.

19. A method as described in claim 15, further comprising administering lactose to said fowl.

20. A method as described in claim 15, further comprising administering a coccidiostat that is not substantially active against gram positive bacteria.

21. A method as described in claim 20, wherein said populations of bacteria are administered with a carrier.

22. A method as described in claim 15, wherein said bacteria are encapsulated.

23. A method as described in claim 15, wherein the step of administering comprises orally administering said populations to said fowl.

24. A method as described in claim 23, wherein the step of administering comprises providing said populations in combination with feed for said fowl.

25. A method as described in claim 23, wherein the step of administering comprises providing said populations in combination with water for said fowl.

26. A method as described in claim 15, wherein the step of administering comprises spraying said populations onto said fowl.

27. A method as described in claim 15, wherein the step of administering comprises contacting said populations with the cloaca of said fowl.

* * * * *